United States Patent
Gleim (10) Patent No.: US 11,147,981 B2
(45) Date of Patent: Oct. 19, 2021

(54) DEVICE FOR INFLUENCING BIOLOGICAL PROCESSES IN LIVING TISSUE

(71) Applicant: BEMER INT. AG, Triesen (LI)

(72) Inventor: Peter Gleim, Triesen (LI)

(73) Assignee: BEMER INT. AG, Triesen (LI)

( * ) Notice: Subject to any disclaimer, the term of this patent is extended or adjusted under 35 U.S.C. 154(b) by 213 days.

(21) Appl. No.: 16/463,672

(22) PCT Filed: Jul. 21, 2017

(86) PCT No.: PCT/EP2017/068503
§ 371 (c)(1),
(2) Date: May 23, 2019

(87) PCT Pub. No.: WO2018/095590
PCT Pub. Date: May 31, 2018

(65) Prior Publication Data
US 2021/0113847 A1 Apr. 22, 2021

(30) Foreign Application Priority Data
Nov. 24, 2016 (DE) .................... 10 2016 122 689.0

(51) Int. Cl.
*A61N 2/00* (2006.01)
*A61N 2/02* (2006.01)

(52) U.S. Cl.
CPC .............. *A61N 2/004* (2013.01); *A61N 2/02* (2013.01)

(58) Field of Classification Search
CPC .................................. A61N 2/004; A61N 2/02
See application file for complete search history.

(56) References Cited

U.S. PATENT DOCUMENTS 3,895,639 A * 7/1975 Rodler .................. A61N 1/323
607/67
4,428,366 A 1/1984 Findl et al.
(Continued)

FOREIGN PATENT DOCUMENTS

DE 42 21 739 A1 1/1993
EP 0 266 807 A2 5/1988
(Continued)

OTHER PUBLICATIONS

International Search Report issued by the European Patent Office in International Application PCT/EP2017/068503 dated Oct. 27, 2017.
(Continued)

*Primary Examiner* — Kaylee R Wilson
(74) *Attorney, Agent, or Firm* — Henry M. Feiereisen LLC (57) ABSTRACT

A device for influencing biological processes in living tissue, in particular a human body, for applying a pulsating magnetic field to at least a part of the tissue, includes a field generation device for generating the pulsating magnetic field and a pulse generator for actuating the field generation device. The pulse generator is designed such that the pulsating magnetic field includes a sequence of primary pulses, the pulse repetition rate of which is between 0.01 and 1000 Hz. The primary pulses are formed by a plurality of superimposed subpulses, wherein the primary pulses are overlaid by secondary pulses. The secondary pulses have a phase shift φ in relation to the primary pulses of $-0.5 > \varphi > 0.5$ and the phase shift φ is not equal to 0.

17 Claims, 8 Drawing Sheets

(56) References Cited

U.S. PATENT DOCUMENTS

| | | | | |
|---|---|---|---|---|
| 5,084,003 | A | * | 1/1992 | Susic ............... A61H 23/0218 600/13 |
| 5,123,413 | A | * | 6/1992 | Hasegawa ............. A61N 1/32 607/2 |
| 5,181,902 | A | | 1/1993 | Erickson et al. |
| 5,480,373 | A | | 1/1996 | Fischer et al. |
| 5,877,627 | A | | 3/1999 | Fischer et al. |

FOREIGN PATENT DOCUMENTS

| | | | |
|---|---|---|---|
| EP | 0 266 907 | A2 | 5/1988 |
| EP | 0 377 284 | A2 | 7/1990 |
| EP | 0 594 655 | B1 | 3/1996 |
| EP | 0 729 318 | B1 | 5/1997 |
| EP | 0 995 463 | B1 | 8/2001 |
| EP | 1 364 679 | A2 | 11/2003 |
| EP | 2 050 481 | A1 | 4/2009 |
| RU | 2017509 | C1 * | 8/1994 |
| WO | WO 96/32159 | A1 | 10/1996 |
| WO | WO 20110023634 | A1 | 3/2011 |

OTHER PUBLICATIONS

K. Spodaryk: "Red blood metabolism and haemoglobin oxygen affinity: effect of electromagnetic fields on healthy adults", in: . Int. World Congress Bio-Electro-Magnetic-Energy Regulation, 2001, pp. 15-19.

Kafka WA Spodaryk K (2003) Effects of extremely weak BEMER 3000 type pulsed electromagnetic fields on red metabolism and hemoglobin oxygen affinity, in: Fizoterapia 11 (3): pp. 24-31.

R. Klopp et al: Einfluss eines pulsierenden elektromagnetischen Feldes mit vasomotorischer Stimulation auf einen eingeschränkten Funktionszustand der Mikrozirkulation. Komplement. Integr. Med Aug. 2007: pp. 47-53.

R. Jelínek,et al: "The electromagnetic BEMER 3000 signal modifies response to teratogens", in: . 3rd Int. World Congress Bio-Electro-Magnetic Energy-Regulation, Bad-Windsheim,Germany, Emphyspace 3, 2002.

M. Preissinger: Verbesserte Wundheilung durch gekoppelte, BEMER 3000 typisch gepulste, Elektromagnetfeld- und LED-Licht-Therapie am Beispiel vergleichender Untersuchungen an standardisierten Wunden nach Ovariektomie bei Katzen (felidae), in: . Edwin Ganster (Hrsg) Österreichische Gesellschaft der Tierärzte (ÖGT) Kleintiertage-Dermatologie, Mar. 2002, Salzburg Congress.

K. Spodaryk: "The effect of extremely weak electromagnetic field treatments upon signs and symptoms of delayed onset of muscle soreness: A placebo controlled clinical double blind study", in: Medicina Sportiva 6, 2002, pp. 19-25.

R. Klopp et al.: Magnetfeldtherapie: Komplementär-therapeutisch sinnvoll oder Unsinn? Stellungsnahme unter Berücksichtigung neuer Forschungsergebnisse mit dem Gerätesystem BEMER 3000, Institut für Mikrozirkulation, Berlin, 2005.

K. Spodaryk et al.: "The influence of extremely weak BEMER 3000 typed pulsed electromagnetic fields on ratings of perceived exertion at ventilatory threshold", in: Marincek et al (eds) Rehabilitation Sciences in the New Millennium Challenge for Multidisciplinary Research. 8th Congress of EFRR, Ljubljana. Medimont International Proceedings, 2004, pp. 279-283.

Kafka et al.: "Application of extreme low frequent (BEMER type) pulsed electromagnetic fields in orthopedics", in: Orthopädische Praxis 41 (1): 2005, 22-24.

Walther et al: "Effects of weak, low frequency pulsed electromagnetic fields (BEMER type) on gene expression of human mesenchymal stem cells and chondrocytes: an in virtro study", in: Electromagnetic Biology and Medicine, Manuscript ID: 257936, 2007.

Michels-Wakili et al: "BEMER 3000 pulsed low-energy electromagnetic fields reduce dental anxiety: a randomized placebo controlled single-blind study", in: . 10th International Congress on Modern Pain Control, Jun. 5-8, 2003 Edinburgh, GB.

Bernatzky et al.: Auswirkung von speziellen, (BEMER-typisch) gepusten elektro-magnetischen Feldern auf Schlafqualität und chronischen Kreuzschmerz des Stütz- und Bewegunsapparates (low back pain): Eine doppelblinde randomisierte Duo Center Studie (Der Schmerz, published), 2007.

M. Gabrys: Pulsierende Magnetfeldtherapie bei zytostalisch bedingter Polyneuropathie. Deutsche Zeitschrift für Onkologie 36, 2004, pp. 154-156.

Carpenter et al: "Biological effects of electric and magnetic elds: sources and mechanism, vol. 1. Beneficial and harmful effects, vol. 2", in: Academic Press, 1994.

M. Quittan et al.: "Klinische Wirksamkeiten der Magnetfeldtherapie-eine Literaturübersicht", in: Acta Medica Austriaca 3, 2000, pp. 61-68.

Matthes Rudiger; "Guidance on determining compliances of exposure to pulsed and complex non sinusoidal waveforms below 100khz with ICNIRP Guidelines", in: The International Commission on Non-Ionizing Radiation Protection ICNIRP Secretariat, Federal Office of Radiation Protection, Institute for Radiation Hygene], 2003.

Rihova et al. "Synergistic effect of EMF-BEMER-type pulsed weak eletromagnetic field and HPMA-bound doxorubicin on mouse EL4 T-cell lymphoma" Journal of Drug Targeting, 2011: 19(10) : 890-899.

R. Klopp: "Vitalmikroskopische und reflexionsspektrometrische Untersuchungen zur Wirkung des Geratesystems "Berner 3000 auf den Funktionszustand der Mikrozirkulatlon" (Vital microscopic and reflection spectrometric studies on the effect of the BEMER 3000 device system on the functional state of the microcirculation)", in: institut für Mikrozirkulation, 2004.

B. Rihova : "Die Wirkung der elektomagnetischen Felder des BEMER 3000 auf das Wachstum des experimentellen Mäuse-EL 4T Zellen-Lymphoms" (The effect of pulse eleotromagnetio field (BEMER 3000) on the growth of a T-cell lymphoma EL4 in conventional C57BL/6 mice and athymic nunu CD1 mice). in: SAMET Kongress,. Interlaken, 2004.

WA Kafka: "The BEMER 3000 Therapy: A new complementary " electro-magnetic drug" effectively supports widespread scattered prophylactic and therapeutic treatments", in: Kochueva E (ed) Achievments in space medicine into health care practice and industry 3rd European praxis matured congress Kople-Druck Sponsored by ESA, DLR & POCKO MOC; 2006.

W Bohn et al.: Energie und Gesundheit: BEMER 3000 Bio-Elektro-Magnetische-Energie- Regulation nach Prof. Dr. Wolf A. Kafka. (Energy and Health BEMER 3000 Therapy Bio-electromagnetic energy regulation according to Prof. Dr. Wolf A. Kafka), Haug Verlag. Stuttgart (Thieme Veracserupoe) 2004. pp. 1-130.

* cited by examiner

DEVICE FOR INFLUENCING BIOLOGICAL PROCESSES IN LIVING TISSUE

CROSS-REFERENCES TO RELATED APPLICATIONS

This application is the U.S. National Stage of International Application No. PCT/EP2017/068503, filed Jul. 21, 2017, which designated the United States and has been published as International Publication No. WO 2018/095590 and which claims the priority of German Patent Application, Serial No. 10 2016 122 689.0, filed Nov. 24, 2016, pursuant to 35 U.S.C. 119(a)-(d).

BACKGROUND OF THE INVENTION

The invention relates to a device for influencing biological processes in living tissue, in particular a human body, by applying a pulsating magnetic field to at least a part of the tissue.

The invention relates to a device and an electric or electromagnetic signal for influencing biological processes in living tissue, in particular a human body, by applying a pulsating electromagnetic field to at least a part of the tissue.

Devices which generate electromagnetic fields and which are routinely used for therapeutic purposes in hospitals, especially in the field of orthopedics, have been known since the beginning of the 70s. The sinusoidal magnetic fields, which were used in semi-invasive methods with pulsating magnetic fields, had a frequency of 2 to 20 Hz and magnetic flux densities between 1 mT and 10 mT. An alternating voltage for generating an external magnetic field was induced at implanted electrodes with the aid of a so-called secondary element.

Furthermore, however, noninvasive treatment without secondary element was also known, in which only very weak electrical currents were induced in the treated body part, which had to be located in the center of the coil. Devices for whole body treatment have also been known since the 70s, in which the field lines are distributed uniformly in the body.

In these treatment forms, a generator is used in this case for actuating a magnetic field generation device, in which the generator actuates the magnetic field generation device such that the magnetic field consists of a plurality of base pulses or primary pulses which have characteristic forms in the time interval and amplitude curve thereof. The pulse frequency is typically between 0 and 1000 Hz. Such a primary pulse can have sinusoidal, trapezoidal, or also sawtooth form (EP 0 594 655 B1 (König Herbert), EP 0 729 318 B1 (Fischer Gerhard, EP-A-0 377 284) or, as in EP 0 995 463 B1 (Kafka Wolf A) can have a sinusoidal modulated field intensity curve which rises exponentially on average, having magnetic flux densities in the range from nanoTesla to several milliTesla. Furthermore, the primary pulses can be composed of a series of chronologically successive sub-pulses, which differ in the amplitudes and/or rising or falling slopes thereof, and thus finally also in the individual duration thereof (cf. EP 0 995 463 B1).

The magnetic fields are frequently generated by one or more electric coils, which are actuated independently of one another (EP 1 364 679 A2, EP-A 0 266 807, EP-A-0 266 907, DE-A 4 221 739, U.S. Pat. No. 5,181,902, WO-A-96/32159, UA-A-4 428 366, EP 0 995 463 B1). Presently, the therapeutic application is typically performed noninvasively for reasons of operative expenditure and the risks linked thereto.

According to common belief, the influence on the biological system is based on a still unknown cooperation of energy components of the magnetic and electrical field components generated by the devices. The physiological and biological interactions triggered by the applied electrical and magnetic field are accordingly based on energetic activation of the reactivity of molecular structures, the naturally provided regulation mechanisms directed to self-preservation. The energetic activation can be triggered directly, magnetically and/or according to the principle of induction (Maxwell equations), and indirectly, by electrical force actions. In contrast, the molecular structures can have ionic, atomic, and molecular form.

For example, EP 0 995 463 B1, describes that an electromagnetic field results in a significant activation of an array of differentiated physical-physiological processes in relation to biological objects to which it is not applied. Thus, for example, The formation of high-energy compounds, in particular of adenosine triphosphate (ATP) and bis-2-3-phospoglycerate (BPG) were observed in human erythrocytes [Spodaryk K (2001) Red blood metabolism and haemoglobin oxygen affinity: effect of electromagnetic fields on healthy adults. In: Kafka W A (ed) 2nd Int Word Congress Blo-Electro-Magnetic-Energy-Regulation. Emphyspace 2: 15-19; Kafka W A, Spodaryk K (2003) Effects of extremely weak BEMER 3000 type pulsed electromagnetic fields on red blood metabolism and hemoglobin oxygen affinity. Fizoterapia 11 (3):24-31].

The improvement of the functional state of the microcirculation, in particular with respect to the circulation behavior (particularly also in the case of diabetes-related circulation illnesses) and the oxygen utilization [Klopp R (2004) Vitalmikroskopische und reflexionsspektrometrische Untersuchungen zur Wirkung des Gerätesystems "BEMER 3000" auf den Funktionszustand der Mikrozirkulation [vital microscopic and reflection-spectrometric studies on the effect of the device system "BEMER 3000" on the functional state of the microcirculation]. Report from the Institut für Mikrozirkulation, Berlin; Klopp R, Niemer W (2007) Einfluss eines pulsierenden elektromagnetischen Feldes mit vasomotorischer Stimulation auf einen eingeschränkten Funktionszustand der Mikrozirkulation [influence of a pulsating electromagnetic field with vasomotor stimulation on a restricted functional state of the microcirculation]. Komplement. Integr. Med 08/2007:47-53].

The acceleration of the process of protective mechanisms, in particular with respect to an accelerated process described in Kopp 2004 of leukocyte immune defense reactions triggered by infection and supported by complex interaction of signal and adhesion molecules.

The protection against chemical stress factors, in particular the reduction of chemically induced (by the teratogen cyclophosphamide) malformations in the ontogenesis of warm-blooded vertebrate embryos (on the model of chicken eggs) [Jelínek R, Bláha J, Dbalý Jaroslav (2002) The electromagnetic BEMER 3000 signal modifies response to teratogens. In: Kafka W A (ed) 3nd Int. World Congress Bio-Electro-Magnetic Energy-Regulation, Bad-Windsheim, Germany, Emphyspace 3].

The improved healing of standard produced wounds [Kafka W A, Preißinger M (2002) Verbesserte Wundheilung durch gekoppeite, BEMER 3000 typisch gepulste, Elektromagnetfeld- und LED-Licht-Therapie am Beispiel vergleichender Untersuchungen an standardislerten Wunden nach Ovariektomie bei Katzen (felldae) [improved wound healing by coupled, BEMER 3000 typical pulsed electromagnetic field and LED light therapy on the example of comparative experiments on standardized wounds after ovarlectomy in cats (Felidae)]. In: Edwin Ganster (Hrsg) Österreichische Gesellschaft der Tierärzte (ÖGT) Kleintlertage-Dermatologie 2-3 Mar. 2002, Salzburg Congress]

Antioxidative regulations in particular with respect to enzymatically and spectrophotometrically determined accelerated reduction conversion rates [Spodaryk K (2002) The effect of extremely weak electromagnetic field treatments upon signs and symptoms of delayed onset of muscle soreness: A placebo controlled clinical double-blind study. Medicina Sportiva 6: 19-25; Klopp R, Niemer W, Pomrenke P, Schulz J (2005) Magnetfeldtherapie: Komplementär-therapeutisch sinnvoll oder Unsinn? Stellungnahme unter Berücksichtigung neuer Forschungsergebnisse mit dem Gerätesystem BEMER 3000 [magnetic field therapy: reasonable for complementary therapy or nonsense? Opinion in consideration of new research results with the device system BEMER 3000], Institut für Mikrozirkulation, Berlin]

Increasing performance in elite level sports [Spodaryk K and Kafka W A (2004) The influence of extremely weak BEMER3000 typed pulsed electromagnetic fields on ratings of perceived exertion at ventilatory threshold. In: Marincek C, Burger H (eds) Rehabilitation Sciences in the New Millennium Challenge for Multidisciplinary Research. 8th Congress of EFRR, Ljubljana. Medimont International Proceedings: 279-283]

Of replication and proliferation mechanisms in particular with respect to a significant reduction of the tumor growth in thymus-free but not in comparatively studied normal mice [Rhova B (2004) Die Wirkung der elektromagnetischen Felder des BEMER 3000 auf das Wachstum des experimentellen Mäuse-EL 4T Zellen-Lymphoms] [the effect of the electromagnetic fields of the BEMER 3000 on the growth of the experimental mouse-EL 4T cell lymphoma], SAMET Kongress, Interlaken; Rihova B, Dbaly J, Kafka W A Exposure to special (BEMER-type) pulsed weak electromagnetic fields does not accelerate the growth of mouse EL4 T cell lymphoma, submitted]

Protein formation and activation in particular with respect to differential up and down regulation of gene-expressed protein quantities. It was possible to show in the scope of a gene chip analysis that the application of the device EP 0 995 463 B1 to stem cells of bone marrow (bone and cartilage cells) Influenced the quantity of the produced proteins differently in relation to untreated: the quantity (expression) of the produced proteins is thus sometimes elevated, sometimes reduced, sometimes it remains uninfluenced (interestingly, inter alia, with respect to the expression of oncogenes) [Kafka W A, Schütze N, Walther M (2005) Einsatz extrem niederfrequent (BEMER typisch) gepulster schwacher elektromagnetischer Felder im Berech der Orthopädie (Application of extreme low frequent (BEMER type) pulsed electromagnetic fields in orthopedics). Orthopädische Praxis 41 (1): 22-24; Walther M, Meyer F, Kafka W A, Schütze N (2007) Effects of weak, low frequency pulsed electromagnetic fields (BEMER type) on gene expression of human mesenchymal stem cells and chondrocytes: an in vitro study. Electromagnetic Biology and Medicine, Manuscript ID: 257936].

Psychovegetative processes, in particular the reduction of the (dentist) anxiety by an electromagnetic local stimulation of the solar plexus immediately preceding dental treatment [Michels-Wakili S and Kafka W A (2003) BEMER 3000 pulsed low-energy electromagnetic fields reduce dental anxiety: a randomized placebo controlled single-blind study. 10th International Congress on modern Pain Control 5-8 Jun. 2003 Edinburgh, GB]

The reduction of lumbar-initiated secondary reactions, in particular the reduction of movement pain, sleeplessness, and anxiety [Bematzky G, Kullich W, Aglas F, Ausserwinkler M, Likar R, Pipam W, H. Schwann H, Kafka W A (2007) Auswirkungen von speziellen, (BEMER-typisch) gepuisten elektromagnetischen Feldem auf Schlafqualltt und chronischen Kreuzschmerz des Stütz- und Bewegungsapparates (low back pain): Eine doppelblinde randomisierte Duo Center Studie [effects of special (BEMER-typical) pulsed electromagnetic fields on sleep quality and chronic low back pain of the support and movement apparatus (low back pain): a double-blind randomized Duo Center study] (Der Schmerz, in press).

The analgesic effect, in particular with respect to the reduction of polyneuropathy pain states as a result of oxidative stress after chemotherapy [Gabrys M (2004) Pulslerende Magnetfeldtherapie bei zytostatisch bedingter Polyneuropathie [pulsating magnetic field therapy in cytostatically-related polyneuropathy]. Deutsche Zeitschrlft für Onkologie 36: 154-156].

have been reported.

Furthermore, in summary, the following have reported on the effects of the application of electromagnetism to biological material Carpenter D O, Aryapetyan S (1994) Biological effects of electric and magnetic fields: sources and mechanism, vol 1. Beneficial and harmful effects, vol 2. Academic Press;

Bohn W, Kafka W A (2004) Energie und Gesundheit: BEMER 3000 Bio-Elektro-Magnetische-Energie-Reguiation nach Prof. Dr. Wolf A. Kafka. [energy and health: BEMER 3000 Bio-electromagnetic energy regulation according to Prof. Dr. Wolf A. Kafka] Haug Verlag, Stuttgart (Thieme Verlagsgruppe): 1-130;

Kafka W A (2006) The BEMER 3000 Therapy: A new complementary "electro-magnetic drug" effectively supports widespread scattered prophylactic and therapeutic treatments. In: Kochueva E (ed) Achievements in space medicine into health care practice and industry 3rd European praxis matured congress KOPIE-DRUCK sponsored by ESA, DLR & POCKO MOC];

Quittan M, Schuhfried O, Wiesinger G F, Fialka-Moser V (2000) Kinische Wirksamkeiten der Magnetfeldtherapie—eine Literaturübersicht [clinical efficacies of magnetic field therapy—a literature overview]. Acta Medica Austriaca 3:61-68;

Matthes Rudiger (2003) Guidance on determining compliances of exposure to pulsed and complex non-sinusoidal waveforms below 100 khz with ICNIRP GUIDELINES. The International Commission on Non-Ionizing Radiation Protection ICNIRP Secretariat, Bundesamt für Strahlenschutz, Institut für Strahlenhygiene [federal office of radiation protection, institute for radiation hygiene], Ingoistädter Landstrasse, D-85764 Oberscheissheim, Germany.

As a result of the differentiated effects on tumor growth and gene expression, the effects cannot be explained with improved microcirculation, but rather confirm and imply the assumption specified at the outset, that the electromagnetically induced biological effects are based on the activation of molecular mechanisms having different causes. It is assumed that the different processes therefore require different amounts of energy for the activation thereof. The distribution of the amplitudes, the formation of the flank slopes, and the superposition of the subpulses therefore receive decisive significance, since the intensity distribution over time is characterized by these parameters. The chronological field intensity distributions therefore receive a similar significance as the structure-activity relationship of medication active ingredients in pharmacy.

Since presently only weak-energy devices are used, furthermore harmful side effects are not to be expected. This is confirmed by reports of the WHO [Electromagnetic Fields (EMF) ff. http://www.who.int/peh-emf/en/; http://www.who.int/topics/electromagnetic_fields/en/;] and a report of a German regulatory authority responsible for the certification of medical products [LGA report 2005], which documented that especially for the device EP 0 995 463 B1—which was estimated to have been used several million times from 1998 to the present according to statistical investigations—no negative health effects were found.

In a refinement described in EP 2 050 481 A1, the intensity curve was adapted over time such that the pulses became more finely adapted to the requirements of the therapy. The optimum shape and sequence of the subpulses individually differs greatly. It is dependent on the type of the tissue subjected to the field, the desired healing success, and the respective individual. The high proportion of the rising or falling flanks sections caused by the plurality of the superimposed subpulses is suspected to have a decisive significance in the stimulation of the exchange processes in the body tissue.

However, as a result of the processes, which are not yet completely understood, in the biological tissue subjected to the electromagnetic field, it has not yet been possible to develop an optimized pulse sequence. All previously known devices for treating the human body therefore do not always result in the desired accelerating effect of the healing process. In particular, it is problematic that in previous devices for achieving a significantly accelerated healing success, the application does not operate sufficiently effectively and a treatment has to be carried out with frequent repetitions. This results in elevated stress of the patient and in significantly higher treatment costs as a result.

It is the object of the invention to provide an improved device and an improved electrical or electromagnetic signal in relation to the prior art, using which more rapid influence, in particular excitation, which is broader in its physiological effect, of biological processes is enabled, by addressing a broad band of electromagnetically activatable molecular structures and thus ensuring a broader physiological breadth of action. The invention is thus directed to the broadest possible effective energetic assistance of the complex interconnected molecular regulation processes. The accompanying therapy concept is thus preventive and is directed to regeneration, preservation, and well-being.

SUMMARY OF THE INVENTION

This object is achieved according to the invention by a device which comprises a pulse generator and a field generation device for generating a pulsating electromagnetic field. The pulse generator is used to actuate the field generation device, wherein the pulse generator actuates the field generation device via suitable current-voltage sequences in such a way that the pulsating electrical or electromagnetic field consists of a plurality of individual pulses formed characteristically with respect to the chronological amplitude curve thereof, and the frequency of which is between 1 and 1000 Hz. Such an individual pulse can be constructed in this case from a superposition of a base pulse rising or falling according to a power function with an array of superimposed pulses each of shorter duration and different form and chronological sequence.

The chronological amplitude curve of such an individual pulse could approximately correspond to the following function:

$$y(x) = \frac{x^a * k * e^{\sin x^b}}{c} + d \qquad (1)$$

therein:
y(x)=denotes magnetic field amplitude within the primary pulse as a function of x;
x=denotes the time curve, wherein x begins again with the same initial value for each primary pulse;
a=denotes a parameter for setting the chronological amplitude curve of each primary pulse (envelope curve);
b=denotes the number of the subpulses;
c=denotes a factor for setting the amplitude;
d=denotes an offset value;
k=denotes a factor for setting the amplitude of the subpulses
where a, b, c≠0.

The parameter a is in this case in a range from 0.1 to 50, preferably in a range from 0.5 to 10, and particularly preferably in a range from 1 to 5. The parameter b is in this case in a range from 0.5 to 50, preferably in a range from 1 to 10, and particularly preferably in a range from 2 to 5.

In the meaning of this patent specification, above-mentioned function (1) is understood as a function which is capable of describing a corresponding amplitude curve, but describes the amplitude curve with the aid of other functions or function components in relation to the illustrated function. These are in particular those functions which contain trigonometric functions, for example, sin x, cos x, arcsin x, or arccos x. These functions or partial functions can replace individual components of the formula.

The device is designed in this case such that the subpulses generated thereby are overlaid by secondary pulses. According to the invention, these secondary pulses have a phase shift φ in relation to the subpulses, which is −0.5<φ<0.5 and wherein the phase shift φ is not equal to 0. In one preferred embodiment, the absolute value of the phase shift φ is greater than 0.1, in one particularly preferred embodiment, the absolute value of the phase shift φ is greater than 0.25.

In relation to the already available devices and the electrical or electromagnetic pulses generated thereby, the pulses generated by the device according to the invention having the additional secondary pulses result in a significantly more rapid excitation of metabolic processes in the affected tissue. The cause for this could be that the pulses overlaid on the base pulses improve the physiological exchange processes via intracorporeal membrane systems, since the additional pulses induce more targeted electromagnetic field peaks according to the induction law (the Maxwell equations) in accordance with the special sequence of the individual pulses then provided, which, for example, via the electromotive force actions originating therefrom, address the generally highly-selective physicochemical reaction mechanisms by way of a corresponding broadband reduction of the activation energies and thus—above all in membrane regions—stimulate the physiological exchange processes. This stimulation results in particular in an elevated $O_2$ utilization.

One particular advantage of the present invention and the electrical or electromagnetic pulses generated thereby is that even with solely local application to living tissue, an excitation of the metabolic processes is to be noted even in the areas of the tissue to which the pulses are not applied.

Advantageous effects may be achieved in various medical applications with such an irradiation. Thus, inter alia, an elevated $O_2$ utilization results in enhanced connective tissue and cartilage formation and additional vascularization.

On the other hand, a mineralization of the connective tissue can also take place due to elevated ion exchange as a result of the bioelectric effect of the induced voltages. The $O_2$ utilization could also promote this. The bone metabolism is very closely linked to the buildup and degradation of cartilage, as shown by the endochondral ossification or the similarly occurring secondary fracture healing. The calcium inflow and outflow kinetics of chondrocytes, which is an important factor in the consolidation of bone fragments, can also be influenced by pulsating of electromagnetic fields. In this case, in particular an enhanced oxygen availability, which is induced by the magnetic field, of the chondrocytes in the cartilage is noticeable and results in elevated synthesis output of the cell. The buildup of the required structures with a minimum of material and energy is facilitated for the organism by the quasi-electrically induced bone formation and the accompanying shape-maintaining and regeneration-promoting effect. An injury, illness, or mere reduction of the elasticity of a bone results in a disturbance of the cell buildup, the matrix production, and the mineralization. Pulsating electromagnetic fields therefore help in this case to compensate for the lack of functional load and the loss of energy and information and to significantly accelerate the bone formation and fracture healing.

Furthermore, the membranes of the membrane systems are influenced directly or by potentials formed in the collagen or only via a change of the microenvironment of the cell upon the application of electrical or electromagnetic pulses. This mechanism is based on an electrochemical transmission, which modifies the cell activity by shifting the ionic atmosphere in the extracellular and thus also in the intracellular space. The primary cause of this is the capacitive charging of the cell membrane by the electrical component of the pulsating electromagnetic fields. The passive ion transportation and diffusion procedures are influenced by the permeability change possible due to the structural shift and charge shift in the membrane, in particular in the area of the pores. The close coupling of surface reaction and transmembrane transportation has the result that above all active transportation systems, such as the Na—K pump, represent an important starting point for the induced energy. Furthermore, the increased Na—K adenosine triphosphate activity can cause an amplified sodium supply by the responsible ion pump. The excitation with an optimum sequence according to the invention of the individual pulses presumably results in the excitation of the active transportation complexes via an elevation of the surface concentration of the corresponding ions.

A device is thus provided, which comprises a pulse generator and a field generation device for generating an electromagnetic field. The pulse generator is used to actuate the field generation device, wherein the pulse generator actuates the field generation device via suitable current or voltage sequences such that the pulsating magnetic field is composed of an array of individually settable individual pulses and a plurality of primary and secondary pulses which are finely graduated with respect to the sequence of individual pulses in such a manner that the spectral composition achieves the greatest possible energy density. Such an individual pulse can be composed in this case of a sequence of primary and secondary pulses, which are uniform on average or rise or fall on average according to a power function with respect to the amplitude thereof, and which are different in the sequence thereof from individual pulses. The resulting pulses can themselves assume a pulsed curve dependent on the selected conditions characterized by the connecting lines of the extremes (envelope curves) of the individual primary pulses.

Further advantageous embodiments of the invention are specified in the dependent claims.

In one embodiment according to the invention, the amplitude curve of the secondary pulse (12) has the following function:

$$y_n(x) = \frac{x^{a_n} * k_n * e^{sinx^{b_n}}}{c_n} + d_n \qquad (2)$$

therein:
$y_n(x)$=denotes a magnetic field amplitude within a secondary pulse as a function of x;
x=denotes the time curve, wherein x begins again with the same initial value for each secondary pulse;
$a_n$=denotes a parameter for setting the chronological amplitude curve of each secondary pulse;
$b_n$=denotes the number of the secondary subpulses;
$c_n$=denotes a factor for setting the amplitude;
$d_n$=denotes an offset value;
$k_n$=denotes a factor for setting the amplitude of the secondary subpulses;
where $a_n$, $b_n$, $c_n \neq 0$.

The parameter a is in this case in a range from 0.1 to 50, preferably in a range from 0.5 to 10, and particularly preferably in a range from 1 to 5. The parameter b is in this case in a range from 0.5 to 50, preferably in a range from 1 to 10, and particularly preferably in a range from 2 to 5.

In the meaning of this patent specification, above-mentioned function (2) is understood as a function which is capable of describing a corresponding amplitude curve, but describes the amplitude curve with the aid of other functions or function components in relation to the illustrated function. These are in particular those functions which contain trigonometric functions, for example, sin x, cos x, arcsin x, or arccos x. These functions or partial functions can replace individual components of the formula.

The resulting pulse $y_r(x)$, which arises from the superposition of the primary pulse and the secondary pulse shifted by a phase shift φ in relation to the primary pulse, may be described by the following equation $$y_r(x) = \frac{x^a * k * e^{sinx^b}}{c} + d + \frac{(x+\varphi)^{a_n} * k_n * e^{sin((x+\varphi)^{b_n})}}{c_n} + d_n \qquad (3)$$

therein:

y(x)=denotes magnetic field amplitude within a primary pulse as a function of x;

x=denotes the time curve, wherein x begins again with the same initial value for each primary pulse;

a=denotes a parameter for setting the chronological amplitude curve of each primary pulse (envelope curve);

b=denotes the number of the subpulses;

c=denotes a factor for setting the amplitude;

d=denotes an offset value;

$a_n$=denotes a parameter for setting the chronological amplitude curve of each secondary pulse;

$b_n$=denotes the number of the secondary subpulses;

$c_n$=denotes a factor for setting the amplitude;

$d_n$=denotes an offset value;

$k_n$=denotes a factor for setting the amplitude of the secondary subpulses;

φ=denotes the phase shift between primary and secondary pulse where a, b, c, $a_n$, $b_n$, $c_n$≠0

The parameter a is in this case in a range from 0.1 to 50, preferably in a range from 0.5 to 10, and particularly preferably in a range from 1 to 5. The parameter b is in this case in a range from 0.5 to 50, preferably in a range from 1 to 10, and particularly preferably in a range from 2 to 5.

In the meaning of this patent specification, above-mentioned function (3) is understood as a function which is capable of describing a corresponding amplitude curve, but describes the amplitude curve with the aid of other functions or function components in relation to the illustrated function. These are in particular those functions which contain trigonometric functions, for example, sin x, cos x, arcsin x, or arccos x. These functions or partial functions can replace individual components of the formula.

In one particular embodiment of the invention, the primary pulses are overlaid with secondary pulses. The secondary pulses have a phase shift φ in relation to the primary pulses, which is between −0.45<φ<0.45, preferably between −0.40<φ<0.40. To be able to set the effect of the secondary pulses, the phase shift φ has to be clear. A quasi-interference between primary and secondary pulse would merely cause a higher amplitude.

In a further embodiment of the invention, the secondary pulses have the same frequency as adjacent primary pulses according to the invention. This has the advantage that the phase shift φ between the primary and the secondary pulses remains constant for adjacent primary and secondary pulse pairs. The envelope curve over primary and secondary pulse thus has the same shape for adjacent primary and secondary pulse pairs. It is thus ensured that the biological tissue experiences the same excitation in each case for each individual primary and secondary pulse pair due to a sequence of primary and secondary pulse pairs.

In a further embodiment of the invention, the secondary pulses have a frequency between 1 and 1000 Hz according to the invention.

In a further embodiment, the invention is designed such that the amplitude of the secondary pulses is multiplied according to the invention by a factor which is between 0.1 times and 10 times the amplitude of the primary pulses adjacent to the secondary pulses. The factor of the amplitude change is, in a further embodiment of the invention, constant for all adjacent primary and secondary pulses, specifically according to the invention in a time interval less than 1 second. This has the result that the shape of adjacent primary and secondary pulse pairs resulting from the superposition of the two individual pulses is identical. An application of pulse sequences according to the invention only results in effective excitation of the biological material to which they are applied due to the repetition of equivalent individual pulses.

In a further special embodiment of the invention, the factor of the reductions of the amplitude of the secondary pulses is equal according to the invention to the factor of the reductions of the amplitude of the primary pulses if the reduction of the primary pulses within a time interval of at most 3 seconds is at least 30% of the maximum amplitude of the primary pulses. In the most promising therapy approaches, during the application of electrical or electromagnetic pulses to the biological tissue, the individual application intervals are interrupted by pauses, in which the amplitude of the pulses is significantly reduced. To ensure this, primary and secondary pulses are reduced uniformly.

In a further embodiment of the invention, the secondary pulses are generated in the same time interval as the primary pulses. Since the secondary pulses only result in significant effects in combination with the corresponding primary pulses, it is advantageous to generate primary and secondary pulses in the same time interval. This time interval, in which the secondary and primary pulses are generated, is greater than 10 seconds in a further embodiment of the invention. According to the invention, the time interval is preferably between 40 seconds and 120 seconds, particularly preferably between 70 seconds and 90 seconds. In a further embodiment of the invention, the time interval in which the secondary pulses are generated is, according to the invention, at least 10% of the time interval in which the primary pulses are generated. A particular advantage results upon the use of the secondary pulses only if they are generated over a certain period of time in parallel to the primary pulses. Therefore, the minimum duration for the application of primary and secondary pulse is to be at least 10 seconds or 10% of the duration of the time interval in which the primary pulses are generated.

In one special aspect of the invention, the frequency of the secondary pulses remains unchanged when the frequency of the primary pulses changes. The frequency of the secondary pulses is, in a further embodiment of the invention, the same as the starting frequency of the primary pulses. In a further embodiment of the invention, the phase shift φ between at least a part of the primary pulses and secondary pulses in the second frequency range of the primary pulses is equal to the phase shift φ between primary pulses and secondary pulses in the first frequency range. Upon a multiplication of the frequency of the primary pulses between first and second time interval, the phase shift φ between the secondary pulse and a primary pulse remains equal. A secondary pulse is simply not associated with every primary pulse, but rather in the case of a frequency doubling, with every second primary pulse, in the case of a frequency tripling, with every third primary pulse, etc.

In one special aspect of the invention, both the phase shift φ and also the frequency of the secondary pulses in the event of a change of the amplitude of the individual pulses from adjacent individual pulses by a factor of less than 0.7 or greater than 1.5 are constant according to the invention. Experience has shown that individual pulses which are significantly changed in the amplitude have a positive effect on the healing action of the application of an electrical or electromagnetic field. To obtain the improved excitation of the biological tissue achieved by the secondary pulses even in the case of individual pulses significantly changed in the amplitude, the secondary pulse has to continue unchanged. The frequency of the secondary pulses therefore remains constant in the event of a significant change of the amplitude of an individual pulse to an adjacent individual pulse. A significant change of the amplitude of an individual pulse is present if the amplitude in relation to an adjacent individual pulse is less by a factor of at least 0.7 or greater by a factor of 1.5 than the adjacent individual pulse.

In a further embodiment of the invention, the ratio of the amplitude of the secondary pulses to the amplitude of the primary pulses in the event of a change of the amplitude of the individual pulses from adjacent individual pulses by a factor of less than 0.7 or greater than 1.5 is constant according to the invention. Experience has shown that individual pulses which are significantly changed in the amplitude have a positive effect on the healing action of the application of an electrical or electromagnetic field. To obtain the improved excitation of the biological tissue achieved by the secondary pulses even in the case of individual pulses significantly changed in the amplitude, the secondary pulse has to continue unchanged. The amplitude of the secondary pulses therefore remains constant in the event of a significant change of the amplitude of an individual pulse to an adjacent individual pulse. A significant change of the amplitude of an individual pulse is present if the amplitude in relation to an adjacent individual pulse is less by a factor of at least 0.7 or greater by a factor of 1.5 than the adjacent individual pulse.

In a further embodiment of the invention, the secondary pulses have a compressed form in comparison to the primary pulses.

An optimization of the effect of the device according to the invention on the organism can be improved by feedback. For this purpose, sensors can be used which measure one or more different physical parameters to optimize the excitation of the body by the electromagnetic pulses. Using the sensors, for example, blood pressure, temperature, pulse, or respiratory volume may be detected and used to optimize the parameters of the device for generating electromagnetic radiation.

BRIEF DESCRIPTION OF THE DRAWING

The invention will be explained in greater detail on the basis of the drawing. In the figures:

FIG. 2a) shows subpulses of a primary pulse, b) shows a primary pulse composed of subpulses, c) shows a simplified illustration of a primary pulse, FIG. 3a) shows a resulting pulse composed of primary pulse and secondary pulse with slight phase shift φ and equal amplitude, b) shows a resulting pulse composed of primary pulse and secondary pulse with slight phase shift φ and different amplitudes, c) shows a resulting pulse composed of primary pulse and secondary pulse with greater phase shift φ and equal amplitude.

DETAILED DESCRIPTION OF PREFERRED EMBODIMENTS

Figure 1:
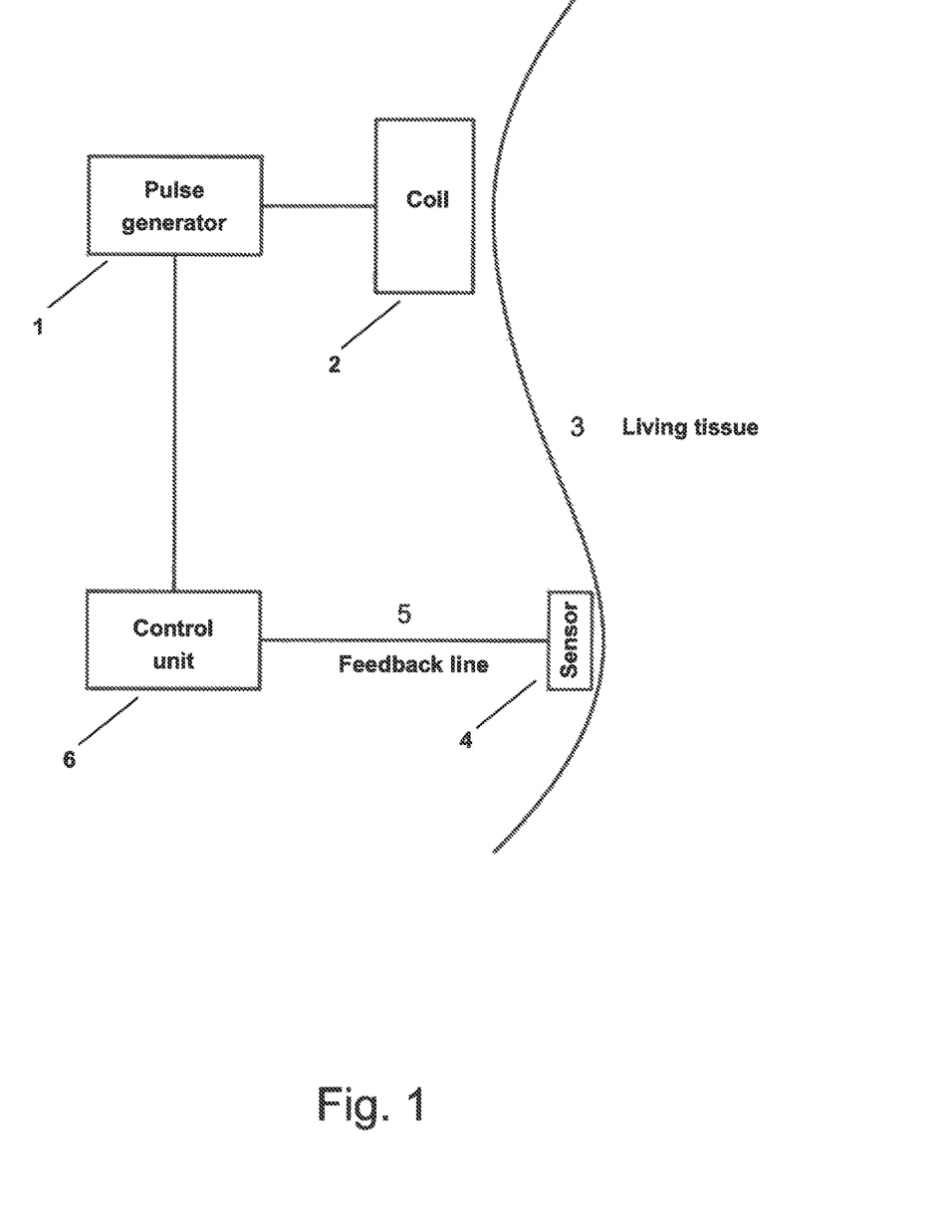
FIG. 1 shows a device according to the invention.

In detail, FIG. 1 shows a device according to the invention, which comprises at least one pulse generator 1, which generates a pulsating magnetic field in the coil 2. The field interacts with the living tissue 3, in particular a body of a patient to be treated. Furthermore, the device according to the invention comprises a sensor, using which physical parameters, for example, the temperature, the blood pressure, the heart rate, or the oxygen content of the blood can be detected. The detected physical parameters are transmitted to a control unit 6 via the feedback line 5. The detected physical parameters can be analyzed and the pulsating magnetic field can be optimized in the generator 1 via the parameters and corresponding algorithms. It is possible to detect and optimize multiple parameters at the same time, in order to set an effective pulsating magnetic field. The control unit 6 can also automatically establish the optimum values for each of the parameters a to d and k as a function of these effects.

Furthermore, the effect of the pulsating magnetic field on the body to be treated can be detected via the sensor 4 and various parameters of the magnetic field can be set in dependence thereon. Such parameters are, for example, the frequency of individual, primary, and secondary pulses and/or subpulses or the amplitude of these pulses. The control unit determines the proportion transmitted to the body to be treated from the differences, in particular in the spectral composition between the field energy generated by the field generation and the magnetic field detected by the sensor. The parameters of the pulsating magnetic field (a to d and k) can be adapted and optimized with respect to the treatment effect via the control unit.

Figure 2:
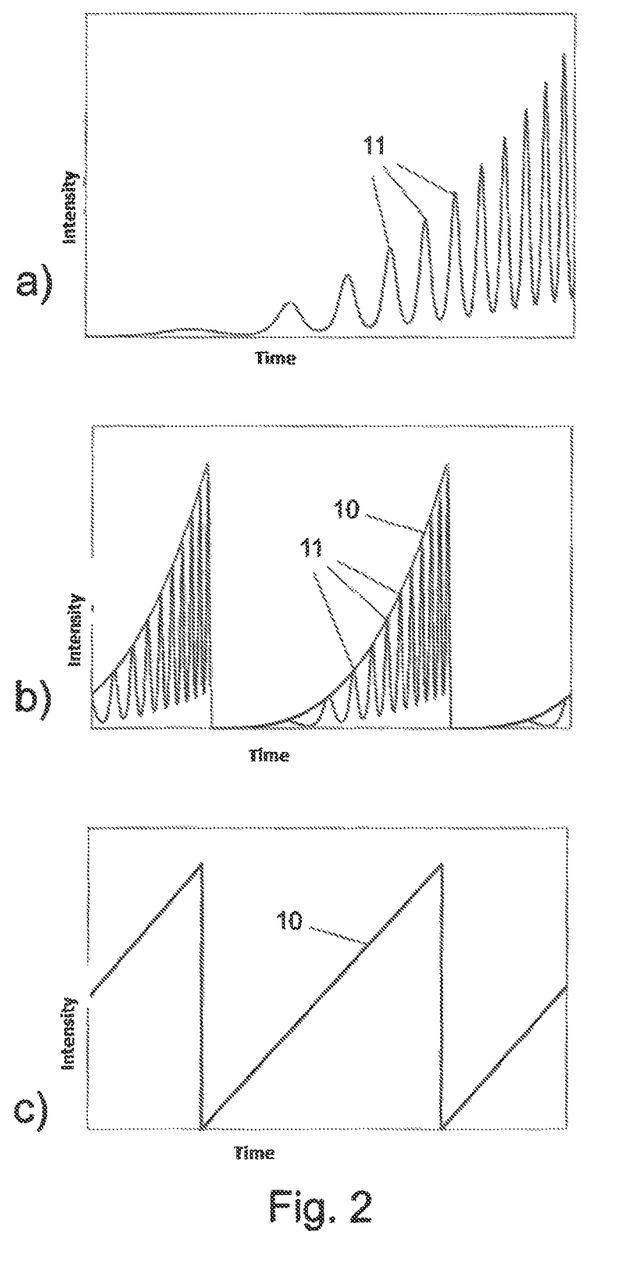

A pulsating magnetic field is generated with the aid of the device according to the invention and the method according to the invention. The magnetic field has a sequence of primary pulses 11, the curve of which corresponds in principle with respect to amplitude and time to the curve shown in FIG. 2b. A simplified form of the amplitude curve is shown in FIG. 2c. The shape of the amplitude curves is dependent on the parameters a to d. Each primary pulse 11 is composed in this case of a sequence of subpulses 13. The maximum intensities of the subpulses 13 rise in the course of a primary pulse 11.

The primary pulses 11, from which the pulsed magnetic field is composed, begin at a time t1 and reach the mean minimum or maximum value thereof. The mean amplitude of the primary pulse 11, and/or the periodically modulated amplitudes therein, rise or fall on average in the course of each primary pulse 11. Increase or decrease takes place according to an exponential function. However, other functions are also conceivable, which describe the mean rise (drop) of the amplitude of a primary pulse 11 within the time. The optimum shape of the sequence of the subpulses 13 is very different individually. It depends on the type of the tissue to which the field is applied, the desired healing success, and the respective individual.

A short "rest time" of specific length can be located between the individual pulses 10, which is presumably required as a result of the relaxation time of the exchange processes and experience has shown leads to better excitation of the living body tissue. The duty cycle between rest time and active pulse time can vary between 3:1 to 1:3 and is preferably approximately 1:1. It is in the order of magnitude of 0 to 200 ms, for example. The duty cycle between rest time (times ta to tb) and pulse repetition duration T is preferably between 0% and 300%. However, in some applications the rest pause can be omitted.

Figure 3:
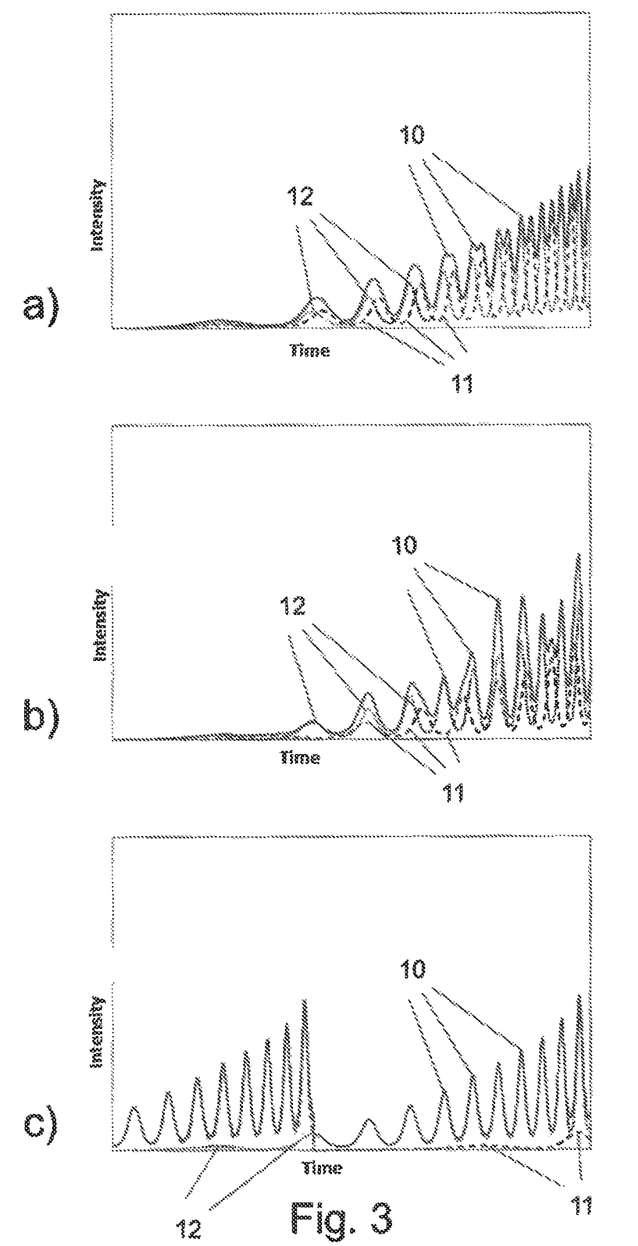

Primary pulses 11 and secondary pulses 12 and the resulting individual pulses 10 arising therefrom for different phase shifts φ are shown in FIG. 3. FIG. 3a) shows a primary pulse 11 composed of the individual subpulses 13a having the parameters a=3, b=3, c=1, d=0, and k=10. The secondary pulse 12 composed of the secondary subpulses 14 has the same parameters here as the primary pulse 11, but is shifted by φ=0.02 in its phase in relation to the primary pulse 11. FIG. 3b) shows the above-described primary pulse 11 together with a secondary pulse 13b shifted by φ=0.1, which is equal in the parameters a, b, c, d, and k to the primary pulse 11, while in FIG. 3c), the phase shift φ of the secondary pulse 12 in relation to the primary pulse 11 is φ=0.45. The further parameters of secondary pulse 12 and primary pulse 11 in FIG. 3c are equal with a=3, b=3, c=1, d=0, and k=10. The figures show that an important instrument is provided with the secondary pulses 12 to decisively influence the characteristic formation of the resulting individual pulses 10, in order to achieve an optimized treatment success. While the overall amplitude of the resulting pulses is equal in FIGS. 3a, 3b, and 3c, the amplitude curves of the resulting individual pulses 10 thus show clear differences. In addition to the total of the maxima of the resulting individual pulse 10, the difference of the amplitudes between maximum and adjacent minimum of the resulting individual pulse 10 or the steepness of the flanks between maximum and adjacent minimum can be varied. In this way the tissue can be addressed very individually with respect to the application and the relaxation.

Figure 4:
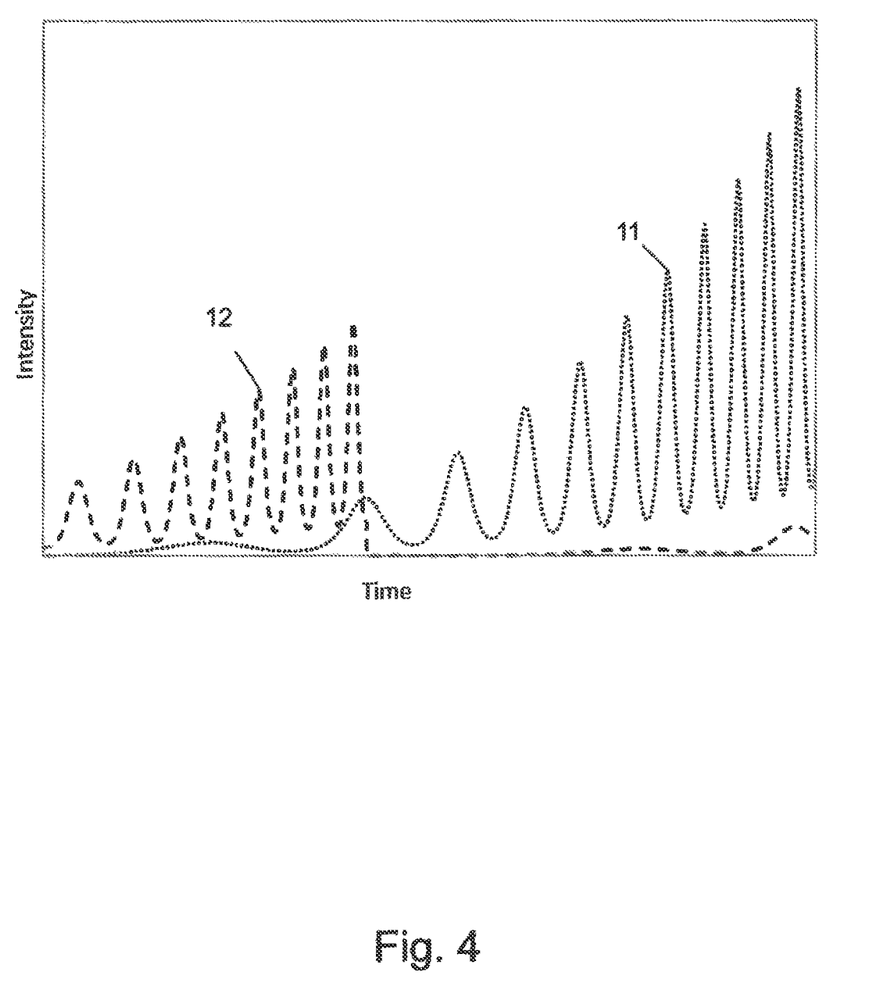
FIG. 4 shows primary and secondary pulses with greater phase shift φ and different amplitudes.

Primary pulse 11 and secondary pulse 13 also do not necessarily have to have the same amplitude. The amplitudes of primary pulse 11 and secondary pulse 12 are variable separately from one another via the parameters c and $c_n$, respectively. This is shown in FIG. 4. While the primary pulse 11 is characterized by the parameters a=3, b=3, c=1, d=0, and k=10, the parameter $c_n$ of the secondary pulse is $c_n$=0.5. The remaining parameters correspond in this exemplary embodiment, with a=3, b=3, d=0, and k=10, to those of the primary pulse 11.

Figure 5:
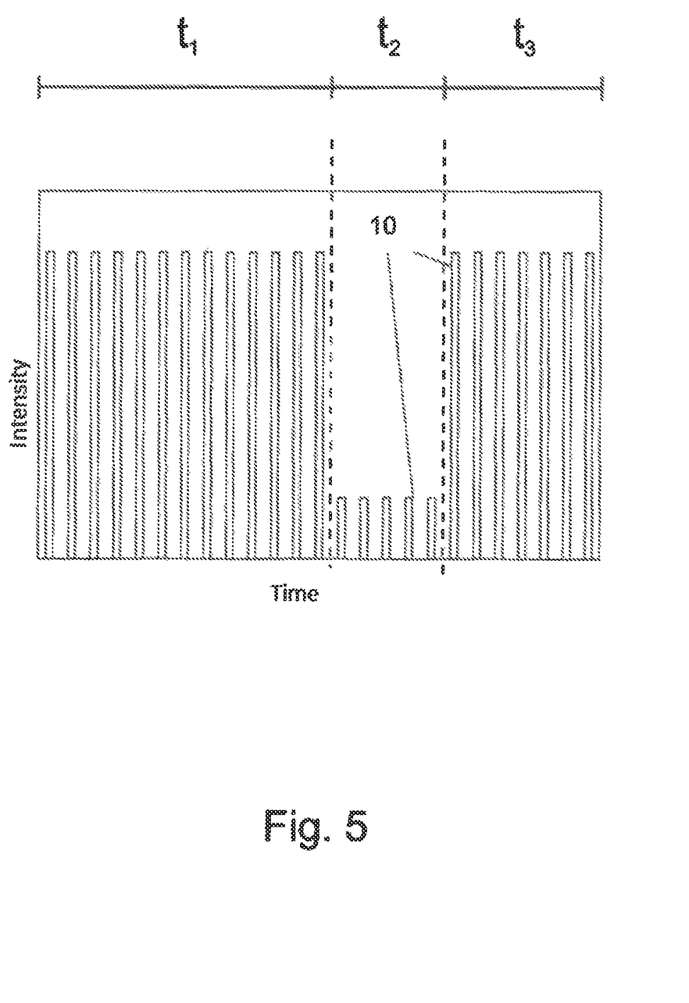
FIG. 5 shows primary pulses interrupted by a pause having uniform amplitude.

Furthermore, the sequence of a majority of the individual pulses 10 can be separated by rest phases 13, cf. FIG. 5. These rest phases have a duration (t2 in FIG. 5) of a plurality of individual pulses, which is at least greater than 10 Individual pulses. The duration of the rest phase t2 is preferably greater than 0.5 seconds, particularly preferably greater than 2 seconds. During these rest phases, the maximum amplitude of the individual pulses is lowered to less than or equal to 30%. A reduction to 0 is also possible. The opportunity for regeneration and relaxation is given to the impinged tissue in this rest phase.

Figure 6:
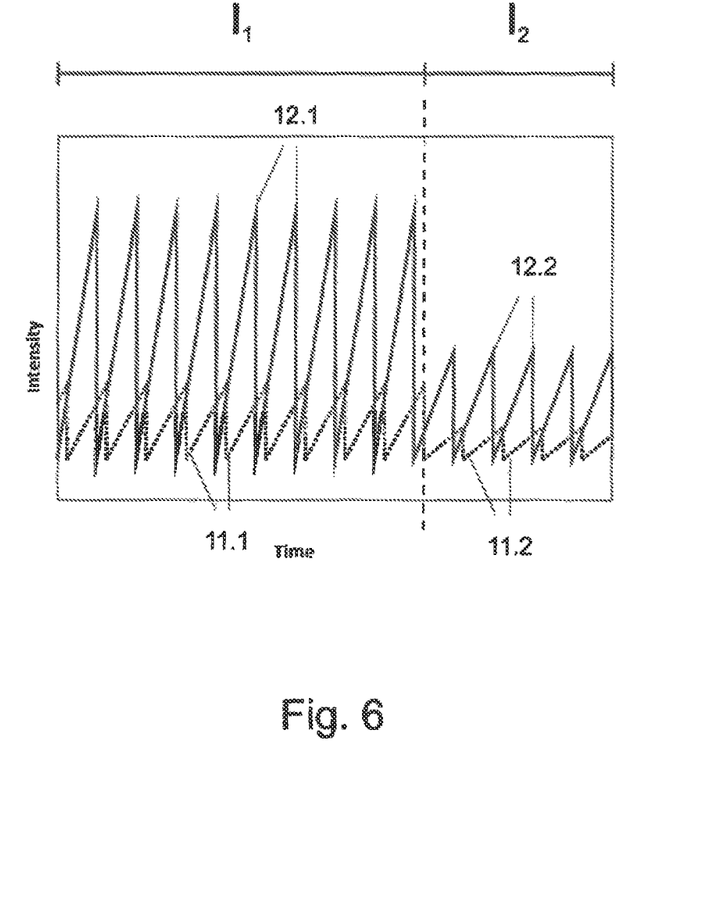
FIG. 6 shows intervals of primary and secondary pulses with proportional change of the amplitude.

FIG. 6 shows a further exemplary embodiment, in which the sequence of the resulting individual pulses 10 is divided into two time intervals. In a first interval, the amplitudes of subpulse 11 and secondary pulse 12 are approximately in a ratio of 3:1. In a second time interval, directly following the first time interval, both the amplitude of the subpulse 11 and also the amplitude of the secondary pulse 12 are reduced by 60%, but the amplitude ratio between the amplitude of the subpulse and the amplitude of the secondary pulse 12 remains the same. In another exemplary embodiment, only the amplitude of the secondary pulse 12 is reduced.

Figure 7:
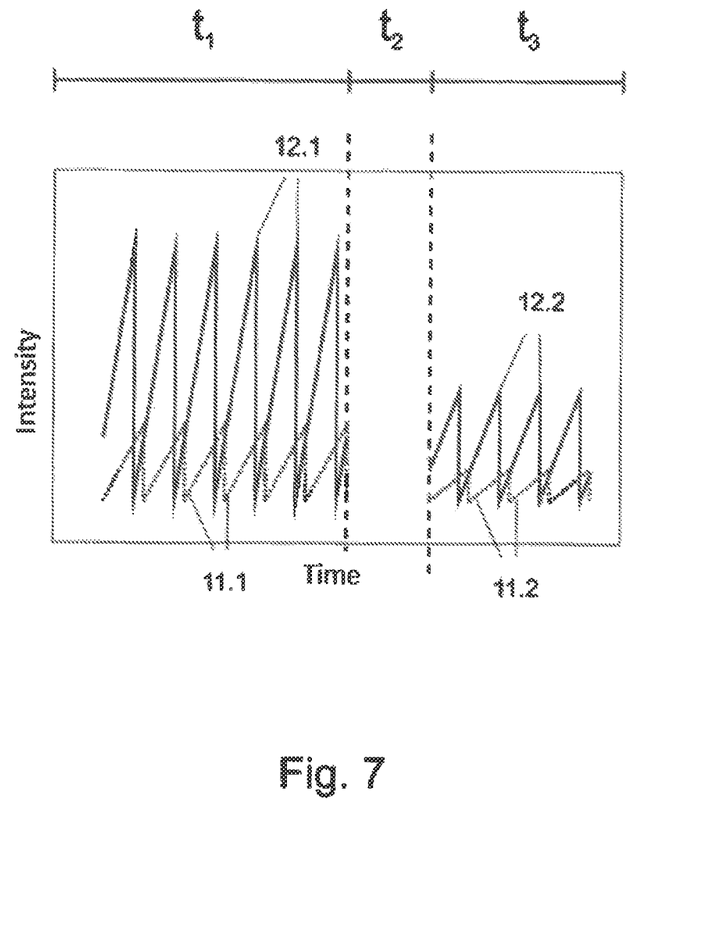
FIG. 7 shows intervals of primary and secondary pulses interrupted by a pause with changed amplitude.

FIG. 7 shows an embodiment of the invention similar to the exemplary embodiment according to FIG. 6. However, the first and the second intervals are interrupted here by a rest phase 13. This rest phase 13 has a duration of multiple resulting individual pulses 10. In this example, there are 10. In this way, the tissue is given the possibility of relaxing during the application phases, which can have a positive effect on the treatment success in some cases.

Figure 8:
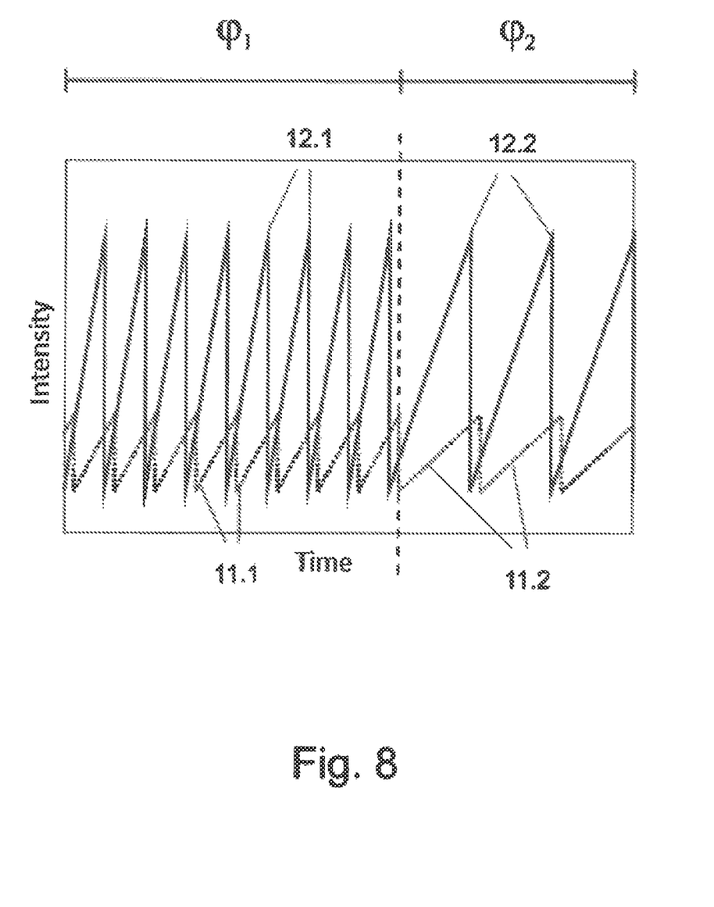
FIG. 8 shows intervals of primary and secondary pulses with proportional change of the frequency and phase shift φ.

A sequence of resulting individual pulses 10 in two successive time intervals is again shown in FIG. 8. In this exemplary embodiment, subpulse and secondary pulse have the same frequency over the entire duration and a constant phase shift φ. In comparison to the first time interval, the frequency of subpulse and secondary pulse in the second time interval is reduced by a factor of 0.5. This dynamic adaptation takes place in this exemplary embodiment to take into consideration the changes in the tissue already occurring due to the application of magnetic pulses in the time interval 1.

In a further exemplary embodiment, primary pulse 11 and secondary pulse 12 have the same frequency at 8 Hz. In a time interval of 10 seconds, the maximum amplitude of primary pulse 11 and secondary pulse 12 is constant. The maximum amplitude of the secondary pulse 12 is at 20% of the maximum amplitude of the primary pulse 11 in this interval. The phase shift φ between secondary pulse 12 and primary pulse 11 is −0.1. In a second time interval, the maximum amplitudes of primary pulse 11 and secondary pulse 12 sink by a factor of 0.05 in comparison to the maximum amplitudes of the first interval. The phase shift φ remains constant. The second time interval is 15 seconds, of which the secondary pulse is transmitted in the first 1.5 seconds.

In a further embodiment of the invention, the primary pulse frequency is 20 Hz and that of the secondary pulse 12 is 25 Hz. In a first time interval of 75 seconds, primary pulse 11 and secondary pulse 12 have a constant maximum amplitude. The maximum amplitude of the secondary pulse 12 is a value higher by a factor of 1.5 than the maximum amplitude of the primary pulse 11. The phase shift p between secondary pulse and primary pulse 11 is 0.05. In a second time interval having a length of 83 seconds, the maximum amplitudes of primary pulse 11 and secondary pulse 12 sink by a factor of 0.1 in comparison to the maximum amplitudes of the first time interval. The phase shift φ remains constant. The secondary pulse 12 is transmitted in the first 21 seconds of the second time interval.

In a further exemplary embodiment according to the invention, the primary pulse frequency and that of the secondary pulse 12 are each 37 Hz. In a first time interval of 900 seconds, primary pulse 11 and secondary pulse 12 have a constant maximum amplitude. The maximum amplitude of the primary pulse 11 is a value higher by a factor of 0.125 than the maximum amplitude of the secondary pulse 12. The phase shift 4 between secondary pulse and primary pulse is 0.42. In a second time interval having a length of 114 seconds, the maximum amplitudes of primary pulse 11 and secondary pulse 12 sink by a factor of 0.28 in comparison to the maximum amplitudes of the first time interval. The phase shift φ remains constant. The frequency of the secondary pulse 12 decreases to 12 Hz in the second time interval.

These primary pulses 11, which are additionally overlaid, by the secondary pulses 12 result in the stimulation of the physiological exchange processes and thus contribute decisively to accelerating the claimed regulation and healing processes. It is important in particular in this case that in addition to the amplitude of these pulses 11, 12, the number of the individual subpulses and secondary subpulses and also the difference between maximum and adjacent minimum can be varied in the course of each resulting individual pulse 10 and, in a significant difference from EP 0 995 463 B1 and EP 2 050 481 A1, the resulting individual pulses are also settable in a significantly more individualized manner and can be graduated substantially more finely with respect to the above-mentioned variables.

The optimum shape and sequence of the resulting individual pulses 10 is dependent on the type of the tissue to which the field is applied, the desired healing success, and the respective individual, and therefore is very different in the individual case. The high proportion and steepness of the rising and falling flanks sections caused by the plurality of the overlaid subpulses 13 and secondary subpulses 14 is presumed to have a decisive significance in the stimulation of the exchange processes in the body tissue.

If specific parameters of the living tissue, in particular of the human body, are detected with the aid of sensors, the course of each resulting individual pulse 10 may be adapted to the actual conditions in such a manner that an optimum stimulation is achieved. For this purpose, the parameters a, b, c, d, k, an, bn, cn, dn, and kn are set as a function of the detected tissue parameters such that application and relaxation are in a ratio optimized for this tissue.

A further optimization of the effect of the present device on the organism can be achieved by feedback. For this purpose, sensors are used, which measure one or more physical parameters around the surroundings of the application, to detect the excitation of the organism by the electromagnetic pulses. Tissue parameters, for example, blood pressure, temperature, pulse, pH value, or respiratory volume may be measured using the sensors and may be used in the sense of an adaptive adaptation of the stimulation to the sensitivity of the tissue to be stimulated to optimize the parameters of the device for generating electromagnetic fields. In particular, the adaptation may be performed dynamically during the treatment, to thus take into consideration short-term changes of the physical state and further optimize the treatment success. This takes place via a feedback loop by which the sensitivity changes in the impinged tissue caused by the excitation itself can be compensated for.

LIST OF REFERENCE SIGNS

1 pulse generator
2 field generation device
3 living tissue
4 sensor
5 feedback line
6 control unit
10 resulting individual pulse
11 primary pulse
12 secondary pulse
13, 13.1, 13.2 subpulse
14, 14.1, 14.2 secondary subpulse
t, $t_1$, $t_2$, $t_3$ time
I, $I_1$, $I_2$ amplitude
$\varphi$, $\varphi_1$, $\varphi_2$ phase shift

What is claimed is:
1. A device for influencing biological processes in living tissue, comprising:
  a field generation device generating a pulsating magnetic field to be applied to at least a part of the tissue, and
  a pulse generator controlling the field generation device and generating a sequence of primary pulses having an amplitude curve defined by equation (1)

$$y(x) = \frac{x^a * k * e^{\sin x^b}}{c} + d \quad (1)$$

and a pulse repetition rate of between 0.01 and 1000 Hz, wherein the primary pulses are composed of a plurality of sub-pulses,
wherein:
x denotes a time;
y(x)=denotes a magnetic field amplitude within the sequence of primary pulses as a function of time x; wherein each primary pulse in the sequence of primary pulses starts with an identical initial magnetic field amplitude value;
a=denotes a parameter for setting the magnetic field amplitude within each primary pulse;
b=denotes a number of the sub-pulses;
c=denotes an amplitude scaling factor of the amplitude curve of the sequence of primary pulses;
d=denotes an offset value;
k=denotes an amplitude scaling factor for the sub-pulses, with a, b, c≠0; and
wherein the pulse generator controlling the field generation device generates secondary pulses having a non-zero phase shift $\varphi$ in relation to the primary pulses of $-0.5\pi < \varphi < 0.5\pi$.

2. The device of claim 1, wherein a magnetic field amplitude curve of the secondary pulses is defined by the equation (2):

$$y_n(x) = \frac{x^{a_n} \cdot k_n \cdot e^{\sin x^{b_n}}}{c_n} + d_n \quad (2)$$

wherein:
x denotes the time;
$y_n(x)$=denotes a magnetic field amplitude within the secondary pulses as a function of time x, wherein each secondary pulse starts with an identical initial magnetic field amplitude value;
$a_n$=denotes a parameter for setting the magnetic field amplitude within each secondary pulse;
$b_n$=denotes a number of secondary sub-pulses;
$c_n$=denotes an amplitude scaling factor of the magnetic field amplitude within the secondary pulses;
$d_n$=denotes an offset value;
$k_n$=denotes an amplitude scaling factor for the secondary sub-pulses, $a_n$, $b_n$, $c_n$≠0.

3. The device of claim 2, wherein the secondary pulses have a frequency identical to a frequency of temporally adjacent primary pulses.

4. The device of claim 3, wherein the amplitude scaling factor of the magnetic field amplitude for all temporally adjacent secondary pulses is constant in a time interval >1 second and the amplitude scaling factor of the magnetic field amplitude for all temporally adjacent secondary pulses is constant in the time interval >1 second.

5. The device of claim 1, wherein the secondary pulses have a frequency between 1-1000 Hz.

6. The device of claim 1, wherein the magnetic field amplitude of the secondary pulses is between 10 times smaller and 10 times larger than the magnetic field amplitude of the primary pulses temporally adjacent to the secondary pulses.

7. The device of claim 1, wherein when the magnetic field amplitude of the primary pulses is reduced to 30% or less of a maximum magnetic field amplitude of the primary pulses, the magnetic field amplitudes of the secondary pulses and of the primary pulses are reduced by an identical amount.

8. The device of claim 1, wherein the secondary pulses are generated in a same time interval as the primary pulses.

9. The device of claim 8, wherein the time interval is greater than 10 seconds.

10. The device of claim 8, wherein a length of the time Interval of the secondary pulses is at least 10% of a length of the time interval of the primary pulses.

11. The device of claim 1, wherein a frequency of the secondary pulses remains unchanged when a frequency of the primary pulses chances.

12. The device of claim 11, wherein the primary pulses have a starting frequency, and wherein the secondary pulses have a starting frequency identical to the starting frequency of the primary pulses.

13. The device of claim 11, wherein the primary pulses have a first frequency range and a second frequency range, and wherein a phase shift between the primary pulses and the secondary pulses in the first frequency range is identical to a phase shift between the primary pulses and the secondary pulses in the second frequency range.

14. The device of claim 1, wherein the phase shift $\varphi$ and a frequency of the secondary pulses remains constant when an amplitude of an individual primary pulse changes from an adjacent individual primary pulse by a factor of <0.7 or >1.5.

15. The device of claim 14, wherein a ratio of the amplitude of the secondary pulses to the magnetic field amplitude of the primary pulses remains constant when the amplitude of an individual primary pulse changes from an adjacent individual primary pulse by a factor of <0.7 or >1.5.

16. The device of claim 1, wherein the secondary pulses have a compressed shape in comparison to the primary pulses.

17. The device of claim 1, wherein the secondary pulses have a non-zero phase shift $\varphi$ in relation to the primary pulses of $-0.45\pi<\varphi<0.45\pi$.

\* \* \* \* \*